(12) United States Patent
Tu

(10) Patent No.: US 10,413,274 B2
(45) Date of Patent: *Sep. 17, 2019

(54) METHOD FOR CONTROLLING WIRELESS INTELLIGENT ULTRASOUND FETAL IMAGING SYSTEM

(71) Applicant: NINGBO YOUCHANG ULTRASONIC TECHNOLOGY CO., LTD, Ningbo (CN)

(72) Inventor: You Chong Tu, Ningbo (CN)

(73) Assignee: NINGBO MARVOTO INTELLIGENT TECHNOLOGY CO., LTD, Cixi, Zhejiang Province (CN)

( * ) Notice: Subject to any disclaimer, the term of this patent is extended or adjusted under 35 U.S.C. 154(b) by 371 days.

This patent is subject to a terminal disclaimer.

(21) Appl. No.: 15/008,582

(22) Filed: Jan. 28, 2016

(65) Prior Publication Data

US 2017/0055944 A1    Mar. 2, 2017

(30) Foreign Application Priority Data

Sep. 2, 2015   (CN) .......................... 2015 1 0554137
Sep. 2, 2015   (CN) .......................... 2015 1 0554138

(51) Int. Cl.
*A61B 8/00* (2006.01)
*A61B 8/14* (2006.01)
*A61B 8/08* (2006.01)

(52) U.S. Cl.
CPC .......... *A61B 8/4427* (2013.01); *A61B 8/0866* (2013.01); *A61B 8/14* (2013.01); *A61B 8/4461* (2013.01); *A61B 8/4472* (2013.01); *A61B 8/4477* (2013.01); *A61B 8/5207* (2013.01); *A61B 8/565* (2013.01)

(58) Field of Classification Search
CPC ....... A61B 8/4427; A61B 8/14; A61B 8/4461; A61B 8/4472; A61B 8/4477; A61B 8/5207

See application file for complete search history.

(56) References Cited

U.S. PATENT DOCUMENTS

| 2004/0015079 A1* | 1/2004 | Berger ................. A61B 8/546 600/437 |
| 2007/0167782 A1* | 7/2007 | Callahan .............. A61B 8/4281 600/443 |

(Continued)

*Primary Examiner* — Joel F Brutus
(74) *Attorney, Agent, or Firm* — Law Offices of Konrad Sherinian LLC

(57) ABSTRACT

A wireless intelligent ultrasound fetal imaging system includes an ultrasound transducer, an ultrasound AFE module, a ZYNQ module, a machine vision module and a mobile device. The mobile device controls the system by transmitting control parameters values to the system over a wireless link. The ZYNQ module receives and applies the parameters, and outputs processing results to a FPGA processor. Controlled by the parameters, the FPGA processor causes the AFE module to transmit ultrasound wave toward a pregnant mother, and receive and process echoing wave. The FPGA processor then conducts imaging processing. The processed image data is then recognized by machine vision module. The processed image data is integrated before it is sent to and displayed the mobile terminal device.

18 Claims, 5 Drawing Sheets

(56) References Cited

U.S. PATENT DOCUMENTS

| | | | |
|---|---|---|---|
| 2007/0239001 A1* | 10/2007 | Mehi | G01S 7/52017 600/437 |
| 2010/0217127 A1* | 8/2010 | Roundhill | A61B 8/08 600/444 |
| 2012/0232398 A1* | 9/2012 | Roham | A61B 8/0866 600/453 |
| 2015/0223778 A1* | 8/2015 | Honjo | A61B 8/0858 600/447 |

* cited by examiner

METHOD FOR CONTROLLING WIRELESS INTELLIGENT ULTRASOUND FETAL IMAGING SYSTEM

CROSS REFERENCE TO RELATED APPLICATIONS

This application claims the benefit and priority of China Patent Application Number 201510554138.0, entitled "METHOD FOR CONTROLLING WIRELESS INTELLIGENT ULTRASOUND FETAL IMAGING SYSTEM," filed Sep. 2, 2015 and which is hereby incorporated by reference in its entirety. This application further claims the benefit and priority of China Patent Application Number 201510554137.6, entitled "WIRELESS INTELLIGENT ULTRASOUND FETAL IMAGING SYSTEM," filed Sep. 2, 2015 and which is hereby incorporated by reference in its entirety. This application also claims the benefit and priority of PCT Patent Application Number PCT/CN2015/091443, entitled "WIRELESS INTELLIGENT ULTRASOUND FETAL IMAGING SYSTEM," filed Oct. 8, 2015 and which is hereby incorporated by reference in its entirety. This application is related to and claims the benefit and priority of U.S. patent application Ser. No. 14/977,711, entitled "WIRELESS INTELLIGENT ULTRASOUND FETAL IMAGING SYSTEM," filed Dec. 22, 2015.

FIELD OF THE DISCLOSURE

The present invention generally relates to an ultrasound imaging system, and more particularly relates to a wireless intelligent ultrasound fetal imaging system operatively coupled to a mobile terminal device. More particularly still, the present disclosure relates to a method for obtaining a fetal image using a wireless intelligent ultrasound fetal image processing system operatively coupled to a mobile device.

DESCRIPTION OF BACKGROUND

A conventional ultrasound imaging system usually includes a probe, a host computer and a display unit. These components are linked by cables for data information transmission. Conventional ultrasound imaging systems have low portability. In other words, bulky conventional ultrasound imaging systems are inconvenient to carry and move around.

In addition, conventional ultrasound imaging systems impose high requirements on their operators. For example, operators of conventional ultrasound imaging systems must go through a professional training process. In particular, three dimensional ("3D") imaging and four dimensional ("4D") imaging features demand even higher requirements on the operators. As used herein, 4D imaging means real-time 3D imaging technologies. In other words, 4D imaging is continuous 3D imaging over the time axis. Moreover, 3D fetal images and 4D fetal images can only be obtained by using extremely expensive conventional ultrasound imaging systems.

With rapid advancements in chip technologies in accordance with Moore's law, chip density becomes higher and higher while chips' physical dimension becomes smaller and smaller. In addition, chips are becoming more powerful at lower power consumption. Accordingly, integrated circuit technologies make small sized ultrasound imaging system equipment possible. Furthermore, rapid developments in machine vision technologies provide certain technological foundation for an intelligent 3D imaging system.

Communication technologies have advanced rapidly in last few decades as well. High speed broadband wireless communication technologies have obtained wide adoption worldwide, and make wireless imaging system possible.

Accordingly, there is a need for a wireless intelligent ultrasound fetal imaging system and a method controlling the system. There is a further need for a handheld wireless intelligent ultrasound fetal imaging system that generates 3D and 4D images.

SUMMARY OF THE DISCLOSURE

Generally speaking, pursuant to the various embodiments, the present disclosure provides a method for controlling a wireless intelligent ultrasound fetal imaging system. The wireless intelligent ultrasound fetal imaging system includes an ultrasound transducer. The ultrasound transducer is adapted to transmit ultrasound wave to a fetus and receive echo wave from the fetus. The system also includes an ultrasonic AFE module operatively coupled to ultrasound transducer. The ultrasonic AFE module is adapted to actuate transmission of the ultrasound wave, reception of the echo wave, and digitize the echo wave, thereby forming digitized signal. The system further includes a ZYNQ module operatively coupled to the ultrasound transducer and the ultrasonic AFE module. The ZYNQ module is adapted to perform image processing on the digitized signal, thereby forming a processed image. Furthermore, the system includes a machine vision module operatively coupled to the ZYNQ module. The machine vision module is adapted to receive the processed image from the ZYNQ module, recognize the processed image to form a recognized image, and send the recognized image to the ZYNQ module. The ZYNQ module integrates the recognized image with a deflection angle of the ultrasound transducer to form an integrated image. Moreover, the system includes a mobile terminal, and a wireless transmission module operatively coupled to the ZYNQ module and the machine vision module. The wireless transmission module is adapted to communicate with the mobile terminal over a wireless communication connection. The mobile terminal receives the integrated image from the wireless transmission module, and displays the integrated image on a screen of the mobile terminal.

BRIEF DESCRIPTION OF THE DRAWINGS

Although the characteristic features of this disclosure will be particularly pointed out in the claims, the invention itself, and the manner in which it may be made and used, may be better understood by referring to the following description taken in connection with the accompanying drawings forming a part hereof, wherein like reference numerals refer to like parts throughout the several views and in which:

A person of ordinary skills in the art will appreciate that elements of the figures above are illustrated for simplicity and clarity, and are not necessarily drawn to scale. The dimensions of some elements in the figures may have been exaggerated relative to other elements to help understanding of the present teachings. Furthermore, a particular order in which certain elements, parts, components, modules, steps, actions, events and/or processes are described or illustrated may not be actually required. A person of ordinary skills in the art will appreciate that, for the purpose of simplicity and clarity of illustration, some commonly known and well-understood elements that are useful and/or necessary in a commercially feasible embodiment may not be depicted in order to provide a clear view of various embodiments in accordance with the present teachings.

DETAILED DESCRIPTION

Figure 1:
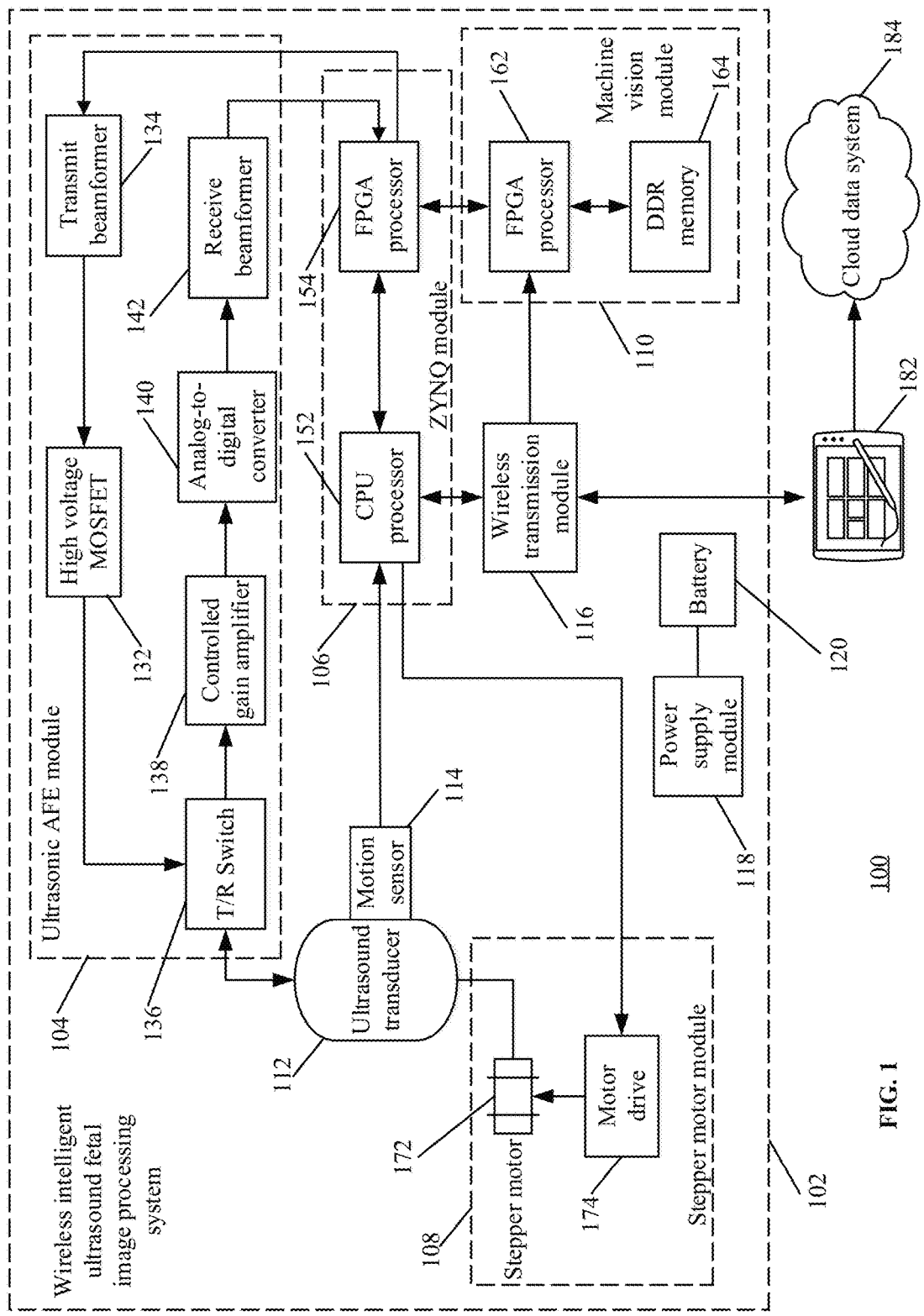
FIG. 1 is a block diagram of a wireless intelligent ultrasonic imaging system in accordance with the teachings of this disclosure.

Turning to the Figures and to FIG. 1 in particular, a simplified block diagram illustrating a wireless intelligent ultrasound fetal imaging system is shown and generally indicated at 100. The wireless intelligent ultrasound fetal imaging system 100 includes a wireless intelligent ultrasound fetal image processing system 102 and a mobile communication device 182 operatively coupled to the processing system 102. The mobile communication device 182 is also referred to herein a mobile terminal, a mobile device and a portable terminal. The mobile terminal 182 can be, for example, a tablet computer (also referred to herein as a PAD), a smartphone, a portable digital assistant device, a portable computer or a personal computer running one or more specialized computer programs (also referred to herein as computer software and computer software applications) written in computer programming languages, such as C, C++, C#, JAVA, OBJECT-C, etc.

The wireless intelligent ultrasound fetal image processing system 102 includes an ultrasound analog front-end ("AFE") module 104, a ZYNQ module 106, a stepper motor module 108, a machine vision module 110, an ultrasound transducer 112 operatively coupled to a motion sensor 114, a power supply module 118 including, for example, a battery 120, and a wireless transmission module 116 for communicating with the mobile terminal 182. The ultrasound transducer 112 emits ultrasonic wave targeting a fetus residing within the body of the carrying mother, and receives echo wave. The ultrasonic AFE module 104 includes a high voltage metal-oxide-semiconductor field-effect transistor ("MOSFET") 132, a transmit beamformer 134, a transmit/receive ("T/R") switch 136, a controlled gain amplifier 138, an analog-to-digital converter ("ADC") 140 and a receive beamformer 142. The ultrasonic AFE module 104 performs digital transmission of ultrasound wave, and reception and processing of echo signal. The ultrasonic AFE module 104 further digitizes the received echo signals.

The ZYNQ module 106 is an electronic module that includes a central processing unit ("CPU") processor 152 and a field-programmable gate array ("FPGA") processor 154. The ZYNQ module 106 performs image processing on the digitized echo signals from the ultrasonic AFE module 104, and generates a processed image. The ZYNQ module 106 then sends the processed image to the machine vision module 110 for recognition. In addition, the ZYNQ module 106 integrates the result of the recognition with the deflection angle data provided by the ultrasound transducer 112, and sends the integrated data to the mobile terminal 182 via the wireless transmission module 116.

The machine vision module 110, including a FPGA processor 162 and a double data rate ("DDR") memory, implements real-time image recognition using comparison of characteristics between images, determines the correct image information without image integration or other processing, and completes tracking and recognition of 3D and/or 4D images. Real-time image recognition using comparison of characteristics between images includes establishing a database of image characteristics, conducting real-time comparison of such databases of images, and finding matching real-time image, which is the effective image.

The mobile terminal 182 controls the ZYNQ module 106, process the data integrated by the ZYNQ module 106, and displays the integrated data on a screen of the mobile terminal 182. For example, the mobile terminal 182 projects, enhances, smooths, rotates the image, zoom and/or glosses the image. In one implementation, the mobile terminal 182 communicated with, for example, a cloud data system 184 (such as a cloud database or cloud data center) for data analysis and sharing. The sharing can be performed using, for example, social networks (such as Facebook) and other forms of Internet based communication means. A user operates the mobile terminal 182 by interacting with the software application running on the mobile terminal device 182.

Figure 2:
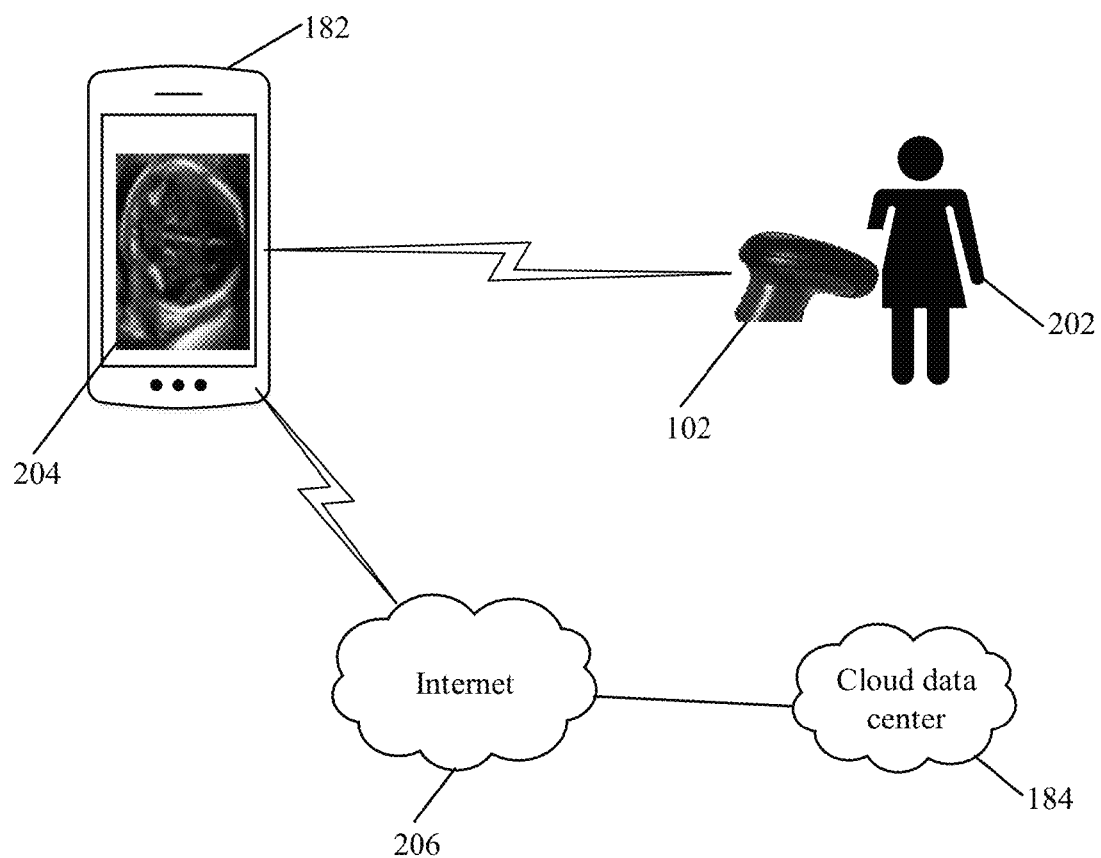
FIG. 2 a block diagram of a wireless intelligent ultrasonic imaging system in accordance with the teachings of this disclosure.

The system 100 is further illustrated by reference to FIG. 2. Referring to FIG. 2, a simplified block diagram of the system 100 is shown. The wireless intelligent ultrasound fetal image processing system 102 is position next to a pregnant mother 202 for scanning her fetus. The system 102 is linked to the mobile terminal device 182 over a wireless connection. A fetal image 204 is displayed on the mobile device 182. The mobile device 182 can upload the image 204 to the cloud 184 over the Internet 206.

Turning back to FIG. 1, the ultrasound transducer 112 achieves displacement through an actuating device. The ultrasound transducer 112 is connected to the motion sensor 114, which obtains deflection angle data of the ultrasound transducer 112. The deflection angle data is additional data for each image frame, and is sent to the ZYNQ module 106 for processing. The deflection angle data can be, for example, a deflection angle. For instance, when the ultrasound transducer 112 receives information indicating a deflection angle of 30 degrees (30°), the motion sensor 114 then causes the ultrasound transducer 112 to make a symmetrical swing. In such a case, the deflection angle 30° is stored in the image frame as a parameter. Such data can be appended to the image frame in a customized format.

Figure 3:
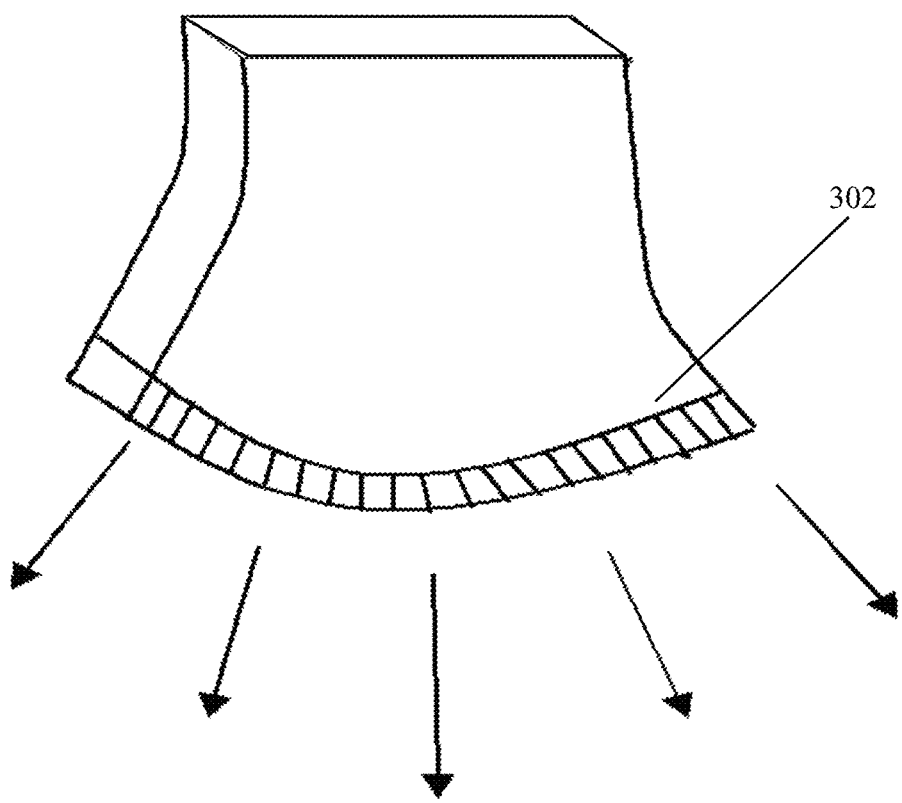
FIG. 3 is a simplified block diagram of the ultrasound transducer in accordance with the teachings of this disclosure.

It should be noted that the ultrasound transducer 112 includes multiple transducer units or two-dimensional array. The multiple units are indicated at 302 in FIG. 3, which shows a simplified block diagram of the ultrasound transducer 112.

The actuating device includes a driving gear and the stepper motor module 108 including a stepper motor 172 and a motor drive 174. The driving gear is disposed between the stepper motor 172 and the ultrasound transducer 112. Through the driving gear, the ultrasound transducer 112 moves with the operation of the stepper motor 172. The motion sensor 114 detects the movement of the ultrasound transducer 112. The ZYNQ module 106, controlled by the mobile terminal 182, controls the starting and stopping of the stepper motor module 108, and other functions of the system 102, such as signal processing.

Signals transmitted by the ultrasonic AFE module 104 is generated by the transmit beamformer 134. In one implementation, the AFE module includes a low-noise amplifier, a variable gain amplifier, an anti-aliasing filter and an analog-to-digital converter for transmitting the signals. The high voltage MOSFET 132 converts the generated signals into high voltage signals. For example, the conversion is made by electrical excitation. The T/R switch 136 functions to excite the ultrasound transducer 112. After the ultrasonic signals are transmitted, the transducer 112 enters into a reception cycle. Through the T/R switch 136, echo signals from the fetus enter the controlled gain amplifier 138. The amplified echo signals are then processed by the ADC 140. The receive beamformer 142 then receives the converted signals from the ADC 140, and converts them into digital beam signals.

Within the ZYNQ module 106, the CPU processor 152 and the FPGA processor 154 are operatively coupled with each other and can communicate with each other. For example, the processors 152-154 exchange data. The FPGA processor 154 controls the transit beamformer 134 to transmit signals, and process digital beam signals output from the receive beamformer 142. The FPGA processor 154 is also operatively coupled to the machine vision module 110. The CPU processor 152 is operatively coupled to the motion sensor 114, the stepper motor module 108 and the wireless transmission module 116.

The FPGA processor 162 and the FPGA processor 154 are operatively coupled to each other and communicate data to each other. The data processed by the FPGA processor 162 is stored in the DDR 164. The mobile terminal 182 communicates with the wireless transmission module 116 using, for example, WiFi, wireless USB, long term evolution ("LTE") fourth generation ("4G"), LTE fifth generation ("5G"), or other wireless communication technologies.

The power supply module 118 provides electric power to other components of the wireless intelligent ultrasound fetal image processing system 102, such as the stepper motor module 108, the ultrasonic AFE module 104, the ZYNQ module 106, the machine vision module 110, the ultrasound transducer 112, etc. The power supply module 118 can include, for example, a high voltage power supply, a lower voltage power supply generating circuit, a battery charge and discharge controller, or a rechargeable battery.

The software application running on the mobile terminal 182 processes data and controls various components of the wireless intelligent ultrasound fetal image processing system 102. Accordingly, compared to conventional fetal imaging systems, the system 100 generates 3D and 4D fetal images faster, imposes lower requirements on the operator's training on the system 100, is a handheld system, and intelligently generates 3D and 4D fetal images by automatically tracking fetal images using the machine vision module 110. Due to its portability, the system 100 can be deployed at hospitals and any other facilities to ease the operation and use of the system 100 by its intended users. In addition, in the system 100, fetal image data and parameters for controlling the system 102 are transmitted wirelessly. Furthermore, the system 100 can be operatively coupled to the Internet for accessing cloud computing power, such as the cloud data center 184. For the example, the terminal 182 can store image data in the cloud data center 184, from where other users (such as a doctor) can access the fetal images generated by the system 100. The generation, transmission, analysis and feedback of fetal images are automatic features of the system 100. In other words, the system 100 can be used and operated by laymen without medical training, and thus dramatically improves productivity.

To operate the wireless intelligent ultrasound fetal imaging system, a user operates the mobile terminal 182 and launches and interacts with the software application running on the mobile terminal 182. The user enters one or more values for control parameters. The software application then controls the mobile terminal 182 to configure the wireless intelligent ultrasound fetal image processing system 102 by setting various control parameters of the system 102. Via the wireless transmission module 116, the CPU 152 receives the parameters' values, and processes the parameters. The CPU 152 also sends relevant processed parameters to the FPGA processor 154. Under the control of such parameters, the FPGA processor 154 controls the transmission of ultrasound wave from the ultrasonic AFE module 104, and reception of echo signal. The ultrasound wave is targeted to the carrying mother of a fetus.

The transmit beamformer 134 generates emission signals, which are converted into high voltage signals by the MOSFET 132. The T/R switch 136 then excites the ultrasound transducer 112 to send the ultrasound wave to the carry mother's body. After the transmission, the ultrasound transducer 112 enters into a reception cycle. Through the T/R switch 136, echo signal from the fetus and the fetus's surrounding area enter the amplifier 138. The amplified signals are converted into digital signals by the ADC 140. The digital signals enter the receive beamformer 142. In response, the beamformer 142 generates beam signals.

To achieve accurate control over 3D data, the ultrasound transducer 112 is operatively coupled to the stepper motor 172. The CPU processor 152 controls the rotation angle of the stepper motor 172 based on parameters received from the mobile terminal 182. The parameters include, for example, swing step interval, maximum step size, minimum step size, scanning center, effective step size and power.

Figure 4:
FIG. 4 is a sample fetal image in accordance with the teachings of this disclosure.

For every stepping unit the stepper motor 172 deflects or moves, one image of the fetus is generated. At the same time, the motion sensor 114 accurately obtains the deflection angle of the ultrasound transducer 112. The deflection angle is a piece of metadata of the image frame, and associated with the image frame. For each particular scanning angle, the ultrasound transducer 112 scans the fetus and a set of data, such as the angle data and the image frames, is collected. The scanning is conducted in a swinging manner. Accordingly, the fetal image takes the shape of a sector as shown in FIG. 4. For a range of scanning angles, multiple sets of data are then collected. As used herein, 3D data refers to the collection of all such data.

Digital beam signal is sent to the FPGA processor 154 for image processing. The output data is then transmitted to the FPGA processor 162 for data recognition processing. The data recognition processing includes, for example, filtering, down sampling, line smoothing, DSC, and fast Fourier transform. The output from the FPGA processor 162 is then sent back to the FPGA processor 154 for data integration. Data integration includes, for example, data construction based on three dimensional imaging algorithm, and perform additional processing on the constructed data. The additional processing includes, for example, trimming, rotation, smoothing, translation in certain direction and zooming. In addition, the constructed data can be further processed for different display configurations.

The CPU processor 152 then, through the wireless transmission module 116, sends the integrated data to the terminal 182, and displays the data on the terminal's 182 screen.

The mobile terminal 182 optionally sends the data (meaning fetal images) to the cloud data center 184 for further analysis and sharing.

Figure 5:
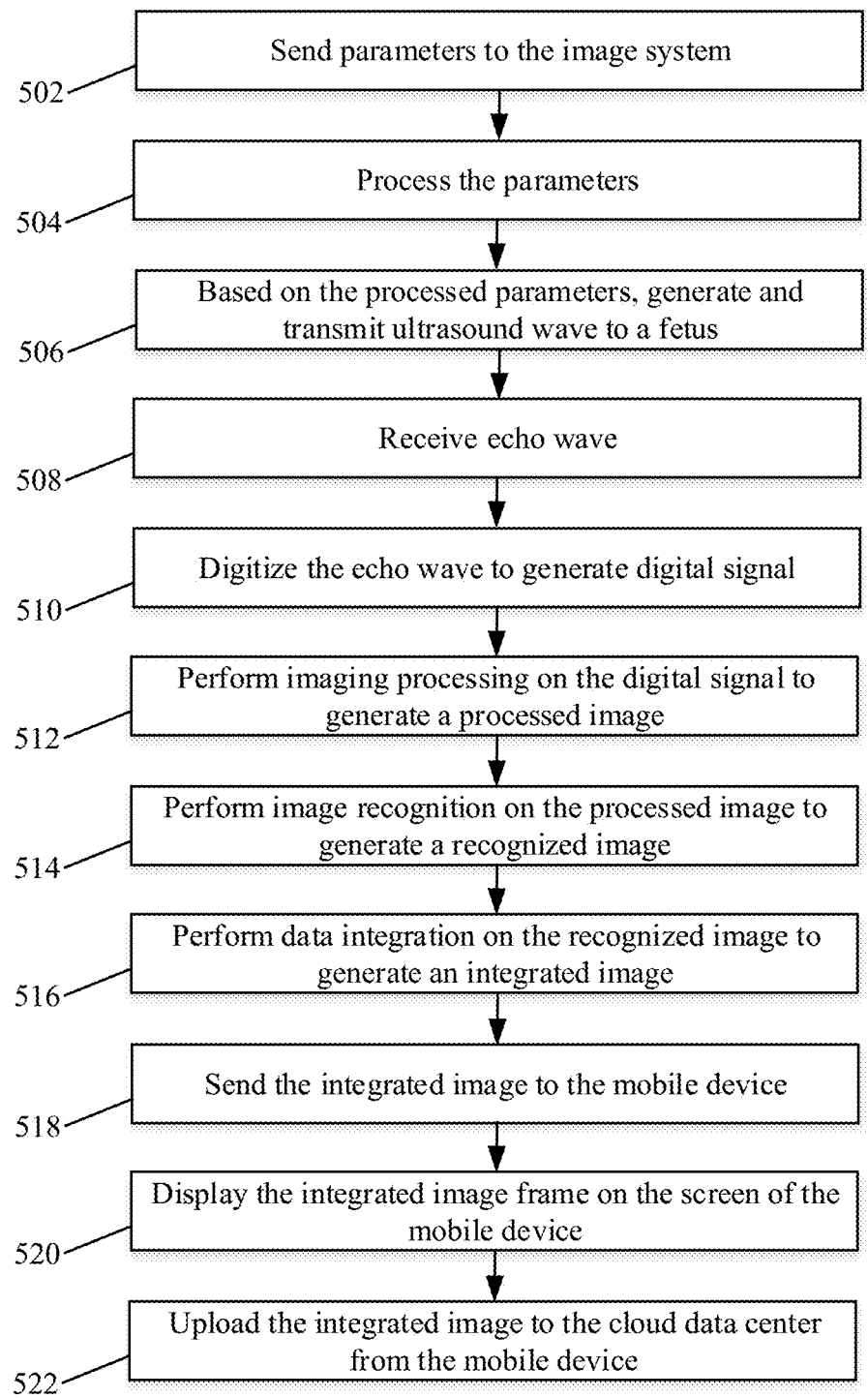
FIG. 5 is a flowchart depicting a process by which wireless intelligent ultrasound fetal image processing system generates a fetal image in accordance with the teachings of this disclosure.

The method for controlling the wireless intelligent ultrasound fetal image processing system is further illustrated by reference to FIG. 5. Turning now FIG. 5, a flowchart depicting a process by which the system 100 generates a fetal image and uploads to the cloud 184 is shown and generally indicated at 500. At 502, the mobile device 182 sends control parameters (also referred to herein as values of parameters) to the system 102. At 504, the system 102 processes the parameters. At 506, based on the processed parameters, the system 102 generates ultrasound wave and transmits such wave to a fetus disposed inside the fetus's mother. At 508, the system 102 receives echo wave. At 510, the system 102 digitizes the echo wave to generate digital signal. At 512, the system 102 performs imaging processing on the digital signal to generate a processed image. At 514, the system 102 performs image recognition on the processed image to generate a recognized image. At 516, the system 102 performs data integration on the recognized image to generate an integrated image. At 518, the system 102 sends the integrated image to the mobile device 182. At 520, the mobile device displays the received image on its screen. At 522, it sends the image to the cloud data center 184 for sharing and further analysis.

Obviously, many additional modifications and variations of the present disclosure are possible in light of the above teachings. Thus, it is to be understood that, within the scope of the appended claims, the disclosure may be practiced otherwise than is specifically described above without departing from the true spirit and scope of the present invention.

The foregoing description of the disclosure has been presented for purposes of illustration and description, and is not intended to be exhaustive or to limit the disclosure to the precise form disclosed. The description was selected to best explain the principles of the present teachings and practical application of these principles to enable others skilled in the art to best utilize the disclosure in various embodiments and various modifications as are suited to the particular use contemplated. It should be recognized that the words "a" or "an" are intended to include both the singular and the plural. Conversely, any reference to plural elements shall, where appropriate, include the singular.

It is intended that the scope of the disclosure not be limited by the specification, but be defined by the claims set forth below. In addition, although narrow claims may be presented below, it should be recognized that the scope of this invention is much broader than presented by the claim(s). It is intended that broader claims will be submitted in one or more applications that claim the benefit of priority from this application. Insofar as the description above and the accompanying drawings disclose additional subject matter that is not within the scope of the claim or claims below, the additional inventions are not dedicated to the public and the right to file one or more applications to claim such additional inventions is reserved.

What is claimed is:

1. A method for obtaining a fetal image using a wireless intelligent ultrasound fetal image processing system, the method comprising:
   i. an ultrasound fetal image processing system receiving a set of parameters from a mobile device, said ultrasound fetal image processing system including:
      (1) an ultrasound transducer;
      (2) an ultrasonic AFE module operatively coupled to said ultrasound transducer;
      (3) a ZYNQ module operatively coupled to said ultrasound transducer and said ultrasonic AFE module;
      (4) a machine vision module operatively coupled to said ZYNQ module; and
      (5) a wireless transmission module operatively coupled to said ZYNQ module and said machine vision module;
   ii. based on set of parameters, said ultrasound transducer generating ultrasound wave;
   iii. said ultrasound transducer transmitting said ultrasound wave to a fetus;
   iv. said ultrasound transducer receiving echo wave corresponding to said ultrasound wave, wherein said ultrasonic AFE module actuates transmission of said ultrasound wave and reception of said echo wave;
   v. said ultrasonic AFE module digitizing said echo wave, thereby forming digitized signal;
   vi. said ZYNQ module performing image processing on said digitized signal, thereby forming a processed image;
   vii. said machine vision module performing image recognition on said processed image to form a recognized image;
   viii. said ZYNQ module performing data integration on said recognized image, thereby forming an integrated image; and
   ix. said wireless transmission module sending said integrated image to said mobile terminal over a wireless communication connection.

2. The method for obtaining a fetal image using a wireless intelligent ultrasound fetal image processing system of claim 1, wherein said mobile terminal receives said integrated image and displays said integrated image on a screen of said mobile terminal.

3. The method for obtaining a fetal image using a wireless intelligent ultrasound fetal image processing system of claim 2, wherein said mobile terminal sends said integrated image to a cloud data center.

4. The method for obtaining a fetal image using a wireless intelligent ultrasound fetal image processing system of claim 3, wherein said mobile terminal sends said integrated image to a cloud data center over the Internet.

5. The method for obtaining a fetal image using a wireless intelligent ultrasound fetal image processing system of claim 1 further comprising:
   i.) said machine vision module receiving said processed image from said ZYNQ module; and
   ii.) said machine vision module sending said recognized image to said ZYNQ module, wherein said ZYNQ module integrates said recognized image with a deflection angle of said ultrasound transducer in forming said integrated image.

6. The method for obtaining a fetal image using a wireless intelligent ultrasound fetal image processing system of claim 1, wherein said ultrasound fetal image processing system further comprising a motion sensor and a stepper motor module, said motion sensor operatively coupled to said ultrasound transducer, said stepper motor module having a stepper motor, said ultrasound transducer moving with the operation of said stepper motor through an actuating device, said motion sensor obtaining a deflection angle of said ultrasound transducer and sending said deflection angle to said ZYNQ module.

7. The method for obtaining a fetal image using a wireless intelligent ultrasound fetal image processing system of claim 6, wherein said actuating device includes a driving gear and said stepper motor module, wherein a starting and a stopping of said stepper motor module is controlled by said ZYNQ module.

8. The method for obtaining a fetal image using a wireless intelligent ultrasound fetal image processing system of claim 6, wherein said ultrasonic AFE module includes a T/R switch, a high voltage MOSFET, a transmit beamformer, a controlled gain amplifier, an analog-to-digital converter and a receive beamformer, wherein:
   i.) said ultrasound wave is generated by said transmit beamformer and amplified by said controlled gain amplifier;
   ii.) said T/R switch excites said ultrasound transducer for transmitting said ultrasound wave;
   iii.) said ultrasound transducer enters a reception cycle after transmission of said ultrasound wave;
   iv.) said controlled gain amplifier amplifies said echo wave, thereby forming amplified signal;
   v.) said analog-to-digital converter converts said amplified signal into digital signal; and
   vi.) said receive beamformer converts said digital signal into beam signal.

9. The method for obtaining a fetal image using a wireless intelligent ultrasound fetal image processing system of claim 8, wherein said ZYNQ module includes a CPU processor and a first FPGA processor, said CPU processor and said first FPGA processor adapted to exchange data, said first FPGA processor controlling said transmit beamformer and said receive beamformer, said CPU processor operatively coupled to said motion sensor, said stepper motor module and said wireless transmission module, said first FPGA processor operatively coupled to said machine vision module.

10. The method for obtaining a fetal image using a wireless intelligent ultrasound fetal image processing system of claim 9, wherein said machine vision module includes a second FPGA processor and a DDR memory, said first FPGA processor communicating with said second FPGA processor for data exchange, said DDR memory storing data output from said second FPGA processor.

11. The method for obtaining a fetal image using a wireless intelligent ultrasound fetal image processing system of claim 6, wherein said wireless transmission module communicates with said mobile terminal over a WiFi connection, a wireless USB connection, a 4G connection or a 5G connection.

12. The method for obtaining a fetal image using a wireless intelligent ultrasound fetal image processing system of claim 6, wherein said ultrasound fetal image processing system further comprising a power supply module providing power for said ultrasound transducer, said stepper motor module, said ZYNQ module, said machine vision module and said ultrasonic AFE module, said power supply module including a high voltage power supply, a lower voltage power supply generating circuit, a battery charge and discharge controller or a rechargeable battery.

13. The method for obtaining a fetal image using a wireless intelligent ultrasound fetal image processing system of claim 6, wherein said mobile terminal is a smart phone, a PAD or a personal computer, and wherein said mobile terminal runs a software application.

14. The method for obtaining a fetal image using a wireless intelligent ultrasound fetal image processing system of claim 1, wherein said ultrasound transducer includes multiple transducer units or a two-dimensional array.

15. A method for obtaining a fetal image using a wireless intelligent ultrasound fetal image processing system, the method comprising:
   i. an ultrasound fetal image processing system receiving a set of parameters from a mobile device;
   ii. based on set of parameters, said ultrasound fetal image processing system generating ultrasound wave;
   iii. said ultrasound fetal image processing system transmitting said ultrasound wave to a fetus;
   iv. said ultrasound fetal image processing system receiving echo wave corresponding to said ultrasound wave;
   v. said ultrasound fetal image processing system digitizing said echo wave, thereby forming digitized signal;
   vi. said ultrasound fetal image processing system performing image processing on said digitized signal, thereby forming a processed image;
   vii. said ultrasound fetal image processing system performing image recognition on said processed image to form a recognized image;
   viii. said ultrasound fetal image processing system performing data integration on said recognized image, thereby forming an integrated image; and
   ix. said ultrasound fetal image processing system sending said integrated image to said mobile terminal over a wireless communication connection.

16. The method for obtaining a fetal image using a wireless intelligent ultrasound fetal image processing system of claim 15, wherein said mobile terminal receives said integrated image and displays said integrated image on a screen of said mobile terminal.

17. The method for obtaining a fetal image using a wireless intelligent ultrasound fetal image processing system of claim 16, wherein said mobile terminal sends said integrated image to a cloud data center.

18. The method for obtaining a fetal image using a wireless intelligent ultrasound fetal image processing system of claim 17, wherein said mobile terminal sends said integrated image to a cloud data center over the Internet.

* * * * *